US006955886B1

(12) United States Patent
Desousa et al.

(10) Patent No.: US 6,955,886 B1
(45) Date of Patent: Oct. 18, 2005

(54) SCINTILLATION PROXIMITY ASSAY FOR THE DETECTION OF PEPTIDOGLYCAN SYNTHESIS

(75) Inventors: Sunita Desousa, Bangalore (IN); Dwarakanath Prahlad, Bangalore (IN)

(73) Assignee: AstraZeneca AB, Sodertalje (SE)

( * ) Notice: Subject to any disclaimer, the term of this patent is extended or adjusted under 35 U.S.C. 154(b) by 0 days.

(21) Appl. No.: 09/341,196

(22) PCT Filed: May 4, 1999

(86) PCT No.: PCT/SE99/00749

§ 371 (c)(1),
(2), (4) Date: Jul. 6, 1999

(87) PCT Pub. No.: WO99/60155

PCT Pub. Date: Nov. 25, 1999

(30) Foreign Application Priority Data

May 15, 1998 (IN) ..................................... 1019/98
Jun. 22, 1998 (SE) ..................................... 9802210

(51) Int. Cl.[7] ..................... G01N 33/567; G01N 33/569
(52) U.S. Cl. ........................... 435/7.2; 435/4; 435/7.1; 435/7.22; 435/7.32; 435/7.37; 435/7.91; 435/7.92; 435/15; 435/24; 435/29; 435/32; 435/34; 435/35; 435/38; 435/39; 435/173.8; 435/177; 435/178; 435/220; 435/260; 435/968; 435/523; 435/524; 435/528; 435/532; 435/534; 435/545; 435/546; 435/172; 435/804; 435/827
(58) Field of Search ............................ 435/6, 7.1, 7.2, 435/7.32, 7.37, 7.92, 15, 24, 29, 32, 35, 38, 435/39, 23, 69.3, 71.1, 183, 184, 4, 7.91, 435/34, 173.8, 177, 178, 220, 260, 968; 436/523, 436/524, 529, 532, 534, 545, 546, 172, 808, 436/827, 528, 804; 536/23.2

(56) References Cited

U.S. PATENT DOCUMENTS 4,568,649 A   2/1986   Bertoglio-Matte .......... 436/534

6,428,971 B1 * 8/2002 Shinabarger et al. ......... 435/15

FOREIGN PATENT DOCUMENTS

| EP | 0890644 | 1/1999 |
| WO | 9426413 | 11/1994 |
| WO | 9615258 | 5/1996 |

OTHER PUBLICATIONS

Mengin-Lecreauz et al., The murG Gene of *Escherichia coli* for the UDP-N-Acetylglucosamine:N-Acetylmuramyl-(Pentapeptide) Pyrophosphoryl-Undecaprenol N-Acetylglucosamine Transferase Involved in the Membrane Steps of Peptidoglycan Synthesis, Journal of Bact, Aug. 1998.*
Kohlrausch et al., Analysis of Murein Precursors during Antibiotic-Induced Lysis of Escherichia, Journal of Bacteriology 173(11): 3425-3431 (Jun. 1991).*
Men et al., Substrate Synthesis and Activity Assay for murG, J. Am. Chem. Soc. 120: 2484-2485 (1998).*
Mengin-Lecreaux et al,. The murG Gene of E. coli for the UPD-N-Acetylglucosamine: N-Acetylmuramyl-(Pentapeptide) Pyrophosphoryl-Undecapernol N-Acetylglucosamine Transferase Involved in the Membrane Steps of Peptidoglycan Synthesis, Journal of Bacteriology 4625-2636 (1991).*
KohlRausch et al., Analysis of Murein Precursors during Antibiotic-Induced Lysis of *E. coli*, Journal of Bacteriology 173 (11): 3425-3431 (1991).*
Men et al., SUbstrate Synthesis and Activity Assay for murG, J. Am. Chem. Soc. 120: 2484-2485 (1998).*
Cook, Drug Discovery Today, vol. 1, No. 7, pp. 287-294 (1996).
Dialog Accession No. 11619936, Abstract from Eid, et al., Journal of Labelled Compounds and Radiopharmaceuticals 41: 705-716 (1998).
Brandish, et al., J. Biol. Chem. 271, 7609-7614 (1996).

* cited by examiner

Primary Examiner—Long V. Le
Assistant Examiner—Gailene R. Gabel
(74) Attorney, Agent, or Firm—White & Case LLP

(57) ABSTRACT

The invention provides a scintillation proximity assay for detecting peptidoglycan synthesis. The assay is especially suitable for high throughput screening of compounds affecting peptidoglycan synthesis.

8 Claims, 4 Drawing Sheets

SCINTILLATION PROXIMITY ASSAY FOR THE DETECTION OF PEPTIDOGLYCAN SYNTHESIS

The present invention relates to a new assay for detecting peptidoglycan synthesis.

BACKGROUND OF THE INVENTION

Peptidoglycan is a major component of the bacterial cell wall that gives the wall its shape and strength. It is unique to bacteria and found in all bacteria, both gram-positive and gram-negative. Peptidoglycan is a polymer of glycan strands that are cross-linked through short peptide bridges. It consists of alternating β1-4 linked residues of N-acetyl glucosamine (GlcNAc) and N-acetyl muramic acid (MurNAc). A pentapeptide chain is attached to MurNAc (MurNAc-pentapeptide) and cross-linking occurs between these peptide chains.

Biosynthesis of peptidoglycan can be divided into three stages: firstly, synthesis of the precursors in the cytoplasm, secondly, transfer of the precursors to a lipid carrier molecule and, thirdly, insertion of the precursors into the cell wall and coupling to existing peptidoglycan.

The precursors synthesised in the cytoplasm are the sugar nucleotides: UDP-N-acetyl-glucosamine (UDP-GlcNAc) and UDP-N-acetylmuramylpentapeptide (UDP-MurNAc-pentapeptide).

The second stage, which occurs in the cytoplasmic membrane, is catalysed by two enzymes and involves synthesis of a disaccharide unit on a lipid carrier, undecaprenyl phosphate. The lipid carrier is also involved in the synthesis of other components of the bacterial cell wall.

The first enzyme catalyses the transfer of phosphoryl-N-acetyl muramyl pentapeptide from UDP-MurNAc-pentapeptide to undecaprenol phosphate with the simultaneous release of UMP. This enzyme is called phospho-N-acetyl-muramyl-pentapeptide translocase (hereafter referred to as "the translocase") and is the product of the gene mraY in *Escherichia coli*. The product, undecaprenol-pyrophosphate-N-acetylmuramylpentapeptide (Lipid-P-P-MurNAc-pentapeptide) or Lipid I or Lipid linked precursor I is the substrate for the second enzyme.

N-acetylglucosaminyl transferase, transfers N-acetylglucosamine from UDP-GlcNAc (with simultaneous release of UDP) to form undecaprenol-pyrophosphoryl-N-acetylmuramylpentapeptide-N-acetylglucosamine or Lipid II or Lipid linked precursor II. This enzyme is also called UDP-N-acetylglucosamine: N-acetylmuramyl(pentapeptide)-P-P-undecaprenol-N-acetylglucosamine transferase (hereafter referred to as "the transferase"). The enzyme is the product of the gene murG in *Escherichia coli*.

The translocase and the transferase enzymes are essential for bacterial viability (see respectively D. S. Boyle and W. D. Donachie, J. Bacteriol. (1998), 180, 6429–6432 and D. Mengin-Lecreulx, L. Texier, M. Rousseaue and J. Van Heijernoot, J. Bacteriol. (1991), 173, 4625–4636).

In the third stage, at the exterior of the cytoplasmic membrane, polymerisation of the glycan occurs. The disaccharide-pentapeptide unit is transferred from the lipid carrier to an existing disaccharide unit or polymer by a peptidogycan transglycosylase (also referred to as a peptidoglycan polymerase) (hereafter referred to as "the transglycosylase"). The joining of the peptide bridge is catalyzed by peptidoglycan transpeptidase (hereafter referred to as "the transpeptidase"). Both enzyme activities, which are essential, reside in the same molecule, the penicillin-binding proteins (or PBPs), as in PBP 1a or 1b in *Escherichia coli*. These are the products of the ponA and ponB genes respectively, in *Escherichia coli*.

On transfer of the disaccharide-pentapeptide unit from the lipid precursor to an existing peptidoglycan chain the lipid is released as a molecule of undecaprenol pyrophosphate. This has to be cleaved by a bacitracin-sensitive undecaprenyl pyrophosphorylase, also called undecaprenol pyrophosphorylase or C55-isoprenyl pyrophosphorylase (hereafter referred to as the "lipid pyrophosphorylase") to generate undecaprenol phosphate which can then re-enter the cycle at the second stage. Since inhibition of this enzyme will inhibit recycling of the lipid precursor it could also inhibit formation of peptidoglycan.

The transglycosylase is usually assayed by radiolabelling one of the sugar molecules and monitoring its incorporation into peptidoglycan. It is a difficult enzyme to assay because the lipid carrier molecule with bound disaccharide is neither simple to make nor water-soluble and, furthermore, the reaction only occurs on a solid phase (e.g. on Whatman 3 mm paper) and so the reaction conditions are difficult to control.

The transglycosylase activity may alternatively be assayed indirectly in a solution phase assay which, whilst being easier to control, requires the use of three of the other key enzymes involved in peptidoglycan synthesis, the translocase (e.g. the mraY gene product), the transferase (e.g. the murG gene product) and the lipid pyrophosphorylase.

In both types of assay, quantification of the products of enzymatic reaction is carried out using paper chromatography in which peptidoglycan stays at the origin and the reactants move away from the origin.

It would be desirable to develop an assay for detecting peptidoglycan synthesis which dispensed with the need for paper chromatography altogether. More particularly, it would be desirable to develop an assay for detecting peptidoglycan synthesis in which the reaction and quantification of the products of reaction could be performed entirely in the solution phase, for example, in a microtitre plate.

BRIEF SUMMARY OF THE INVENTION

In accordance with the present invention, there is therefore provided an assay for detecting peptidoglycan synthesis, which comprises the steps of:

(1) incubating a reaction mixture comprising in aqueous medium a UDP-N-acetylmuramylpentapeptide (UDP-MurNAc-pentapeptide), radiolabelled UDP-N-acetyl glucosamine (UDP-GlcNAc), a source of divalent metal ions, a source of undecaprenyl phosphate, a source of peptidoglycan, a source of translocase enzyme (e.g. the *E. coli* mraY gene product), a source of transferase enzyme (e.g. the *E. coli* murG gene product), a source of transglycosylase enzyme, a source of transpeptidase enzyme (e.g. *E. coli* PBP 1a or PBP 1b) and a source of lipid pyrophosphorylase, under conditions suitable for peptidoglycan synthesis;

(2) adding a divalent metal ion chelator compound to the reaction mixture of step (1);

(3) adding lectin-coated beads impregnated with a fluorescer to the reaction mixture of step (2); and (4) measuring light energy emitted by the fluorescer.

DETAILED DESCRIPTION OF THE INVENTION

Figure 1:
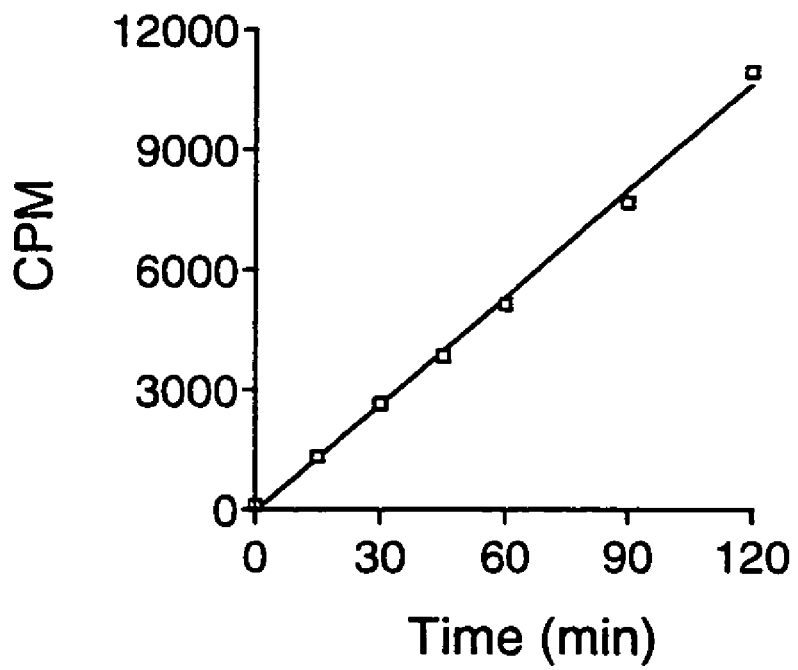
FIG. 1 is a graph showing the counts per minute (cpm) versus time based on the readings taken from the 100% controls.
Figure 2:
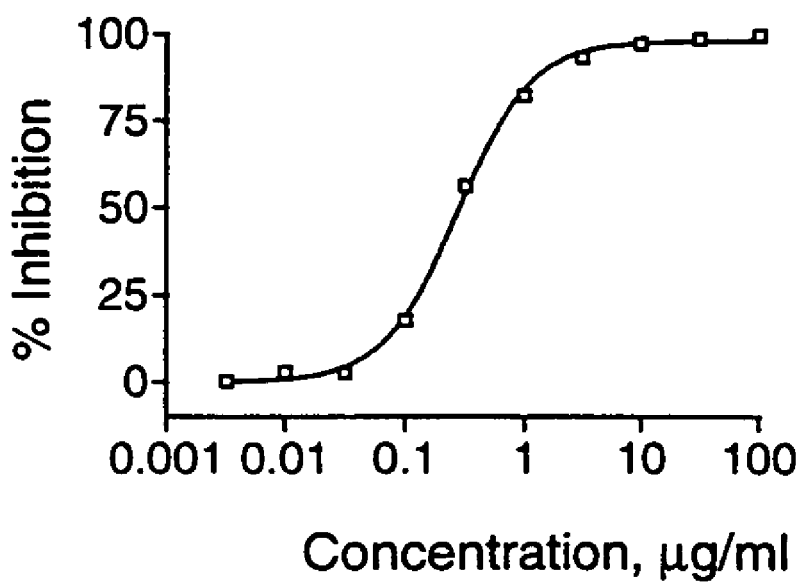
FIG. 2 is a graph showing the percentage inhibition of translocase (and thus peptidoglycan synthesis) versus Tunicamycin concentration.
Figure 3:
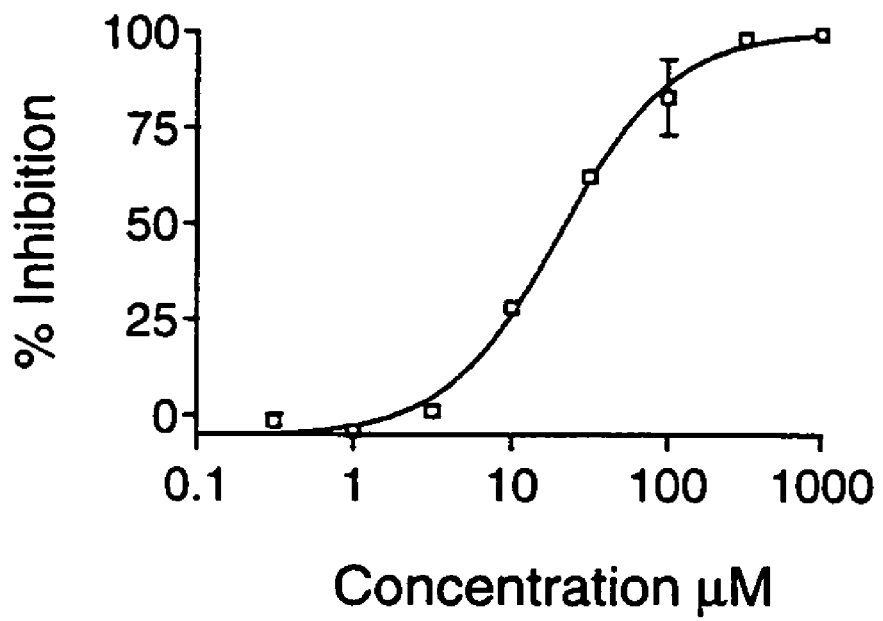
FIG. 3 is a graph showing the percentage inhibition of transglycosylase (and thus peptidoglycan synthesis) versus Vancomycin concentration.
Figure 4:
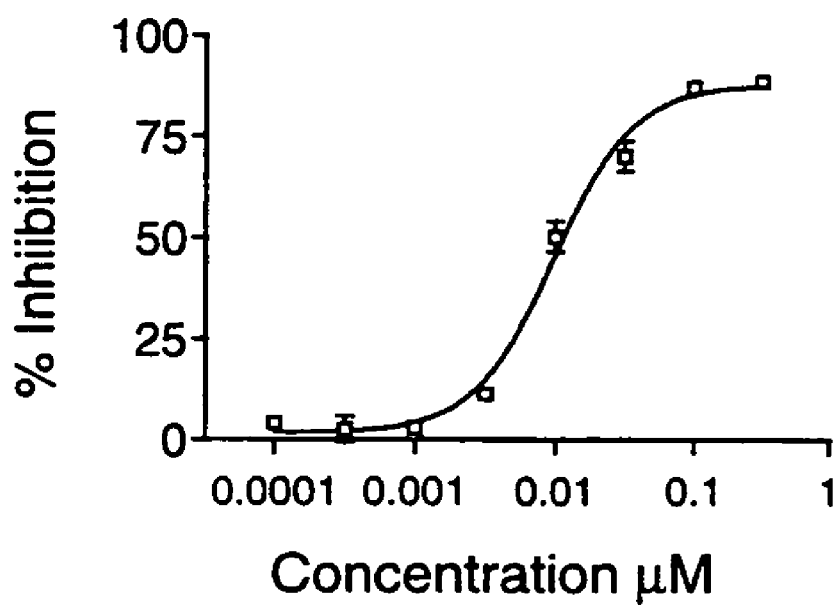
FIG. 4 is a graph showing the percentage inhibition of transglycosylase (and thus peptidoglycan synthesis) versus Moenomycin concentration.
Figure 5:
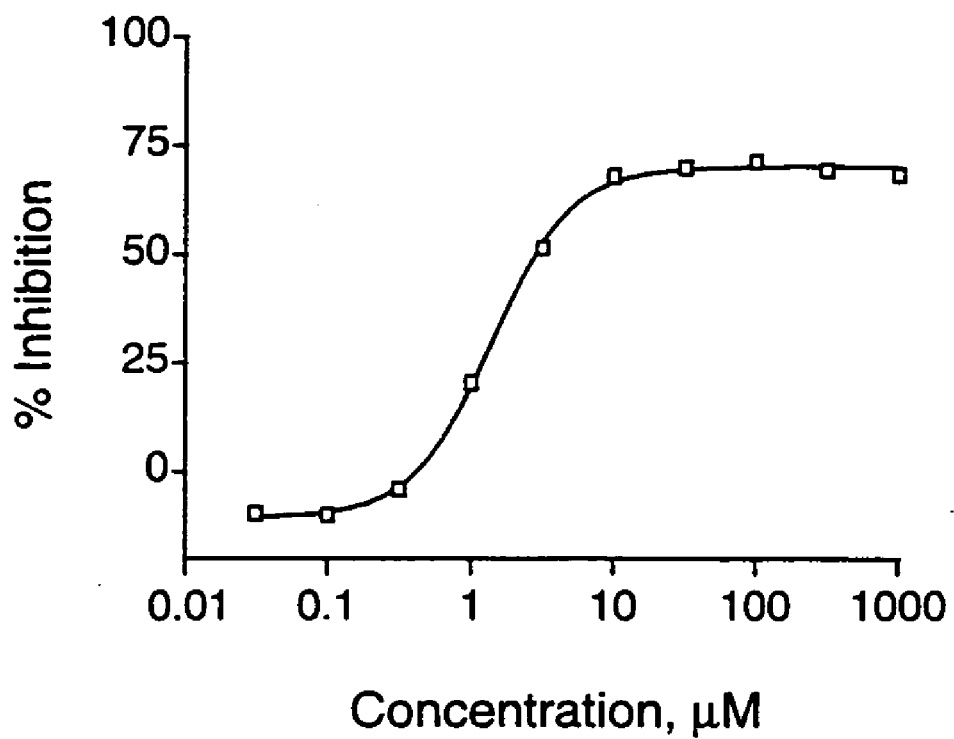
FIG. 5 is a graph showing the percentage inhibition of transpeptidase (and thus peptidoglycan synthesis) versus Penicillin G concentration.
Figure 6:
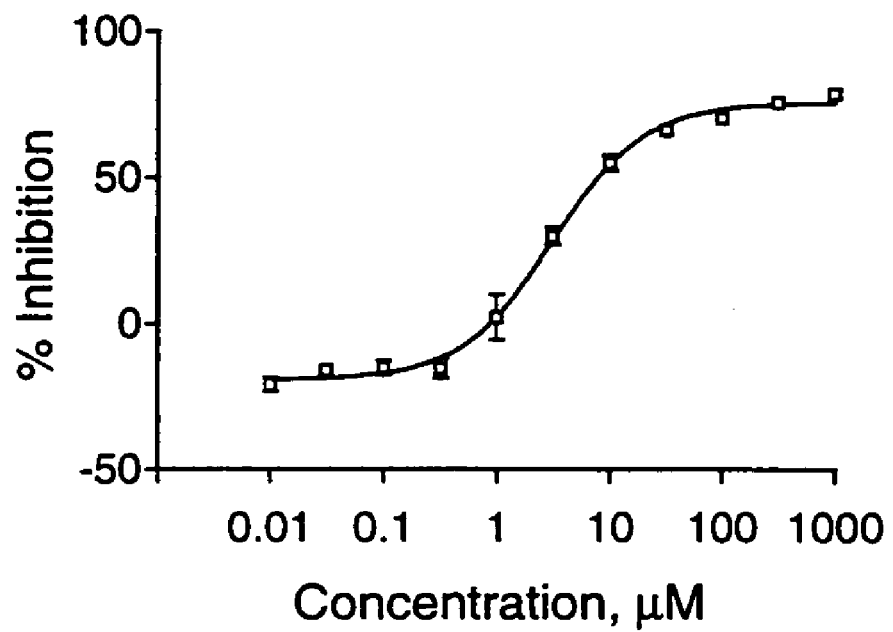
FIG. 6 is a graph showing the percentage inhibition of transpeptidase (and thus peptidoglycan synthesis) versus Ampicillin concentration.
Figure 7:
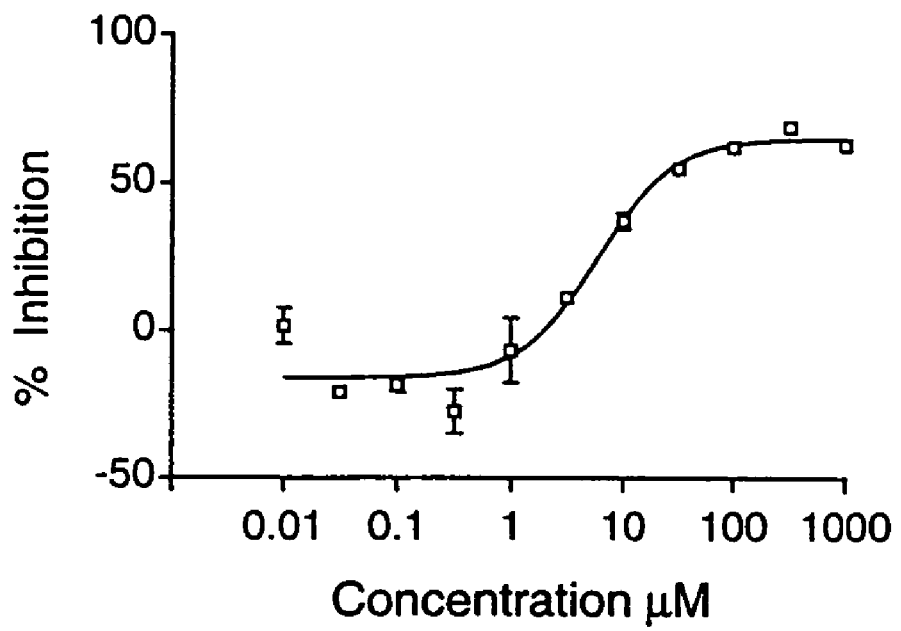
FIG. 7 is a graph showing the percentage inhibition of transpeptidase (and thus peptidoglycan synthesis) versus Cephaloridine concentration.
Figure 8:
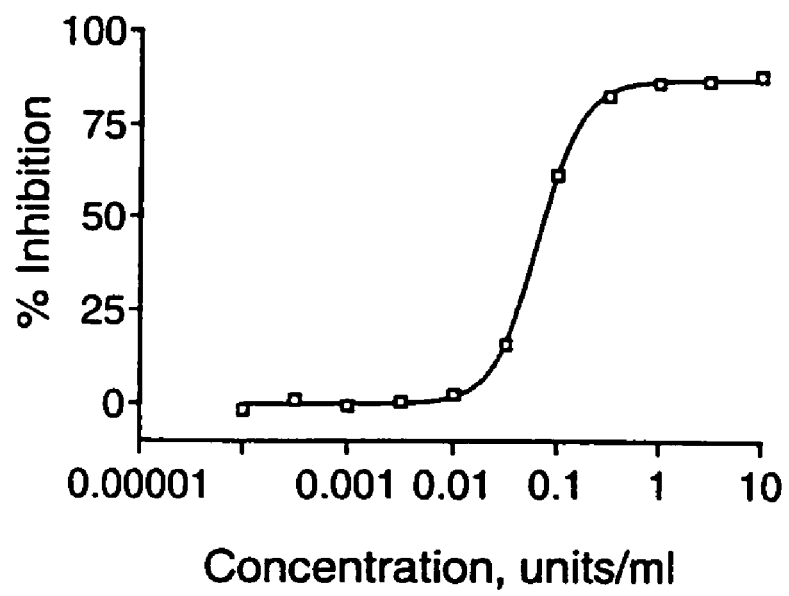
FIG. 8 is a graph showing the percentage inhibition of lipid pyrophosphorylase (and thus peptidoglycan synthesis) versus Bacitracin concentration.

In the context of the present specification, it should be understood that the abbreviation "UDP" refers to uridine (5'-)diphosphate.

The assay according to the present invention is very conveniently carried out on 96-well microtitre plates, thereby enabling a fast, simple and reproducible way of measuring peptidoglycan synthesis. In step (1), the UDP-MurNAc-pentapeptide used may be any of those usually present in naturally-occurring peptidoglycans and is conveniently purified from bacteria or made enzymatically with precursors from bacteria, e.g. by methods similar to that described by T. den Blaauwen, M. Aarsman and N. Nanninga, J. Bacteriol. (1990), 172, 63–70). A preferred UDP-MurNAc-pentapeptide to use is UDP-MurNAc-L-alanine-γ-D-glutamic acid-m-diaminopimelic acid-D-alanine-D-alanine from *Bacillus cereus*. The purified UDP-MurNAc-pentapeptide may also contain a certain amount of the tripeptide and tetrapeptide analogues and these may also participate effectively in the peptidoglycan synthesis reaction.

The concentration of UDP-MurNAc-pentapeptide used will typically be in the range from 50 µM, preferably from 75 µM, to 300 µM, preferably 200 µM, more preferably 100 µM, per well of the microtitre plate.

As radiolabelled UDP-N-acetyl glucosamine, it is convenient to use tritiated UDP-N-acetyl glucosamine (UDP-[3H] GlcNAc, commercially available from NEN-Dupont), preferably in a concentration of from 0.25 to 25 µM per well of the microtitre plate, with radioactivity in the range from, e.g., 0.07 µCi to 2.00 µCi per well, preferably from 0.10 µCi to 1.00 µCi per well, and more preferably from 0.10 µCi to 0.5 µCi per well.

The divalent metal ions used are preferably magnesium ions. A suitable source of magnesium ions is magnesium chloride.

The membranes of *Escherichia coli* bacteria may conveniently be used and indeed are preferred as a source of undecaprenyl phosphate, peptidoglycan, translocase enzyme, transferase enzyme, transglycosylase enzyme, transpeptidase enzyme and lipid pyrophosphorylase enzyme. The quantity of membranes used will typically be in the range from 1 to 20 µg, particularly from 4 to 6 µg, protein per well of the microtitre plate. The membranes may be prepared by methods known in the art.

The aqueous medium used in step (1) is preferably a buffer solution, e.g. of Tris[hydroxymethyl]aminomethane hydrochloride ("Tris-HCl"), having a pH of about 7.5. Tris-HCl is commercially available from the Sigma-Aldrich Co. Ltd.

If the assay is intended to be used as a screen for identifying anti-bacterial compounds that are antagonists of the translocase, transferase, transglycosylase, transpeptidase or lipid pyrophosphorylase enzymes, the reaction mixture of step (1) may further comprise one or more test compounds in varying concentrations. Since the transglycosylase and transpeptidase enzymes are essential for bacterial growth and are located on the cell surface, these enzymes are regarded as especially good targets for the development of anti-bacterial drugs as the drugs would not need to enter the bacterial organism through the cell wall and therefore the problems of cell wall permeability and also drug resistance brought about by changes in cell wall permeability are avoided.

The reaction mixture of step (1) is maintained at a temperature at or about 37° C. for a period of 0.5 to 4 hours, e.g. 1.5 hours, under conditions suitable for peptidoglycan synthesis to occur.

Peptidoglycan synthesis is terminated in step (2) by the addition of a suitable amount of a divalent metal ion chelator compound, e.g. ethylenediaminetetraacetic acid (EDTA) which is commercially available from the Sigma-Aldrich Co. Ltd. The concentration of the chelator compound will of course depend on the particular chelator compound used and should be sufficient to chelate all the divalent metal ions; in the case of EDTA the concentration will typically be about 15 mM per well of the microtitre plate.

In step (3), preferred lectin-coated beads impregnated with a fluorescer to use are those described in U.S. Pat. No. 4,568,649 and European Patent No. 154,734. The beads (known as "Scintillation Proximity Assay" (or SPA) beads) are commercially available from Amersham Inc. Most preferred are wheatgerm agglutinin-coated SPA beads which are capable of binding sugar molecules, specifically N-acetyl glucosamine. Thus, through the binding of N-acetyl glucosamine to the SPA beads, radiolabelled peptidoglycan formed in step (1) is brought into close proximity with the fluorescer which becomes activated by the radiation energy, resulting in the emission of light energy which is subsequently measured in step (4).

The beads which are conveniently added in the form of an aqueous suspension are contacted with the reaction mixture of step (2) for a period of 3 hours or more (e.g. overnight) before the plate is "counted" in step (4), e.g., in a "Microbeta Tilux" counter.

Apart from screening for anti-bacterial compounds as mentioned above, the assay according to the invention may, since it is sensitive to β-lactam antibiotics, be used alternatively to screen for novel β-lactams and also to measure the concentration of β-lactam antibiotics or to measure the activity of β-lactamases, enzymes that degrade β-lactams. In this way, the assay can be used as a diagnostic to detect disease-causing bacteria that are resistant to β-lactams because of the production of β-lactamases. Further, the assay may be used to identify inhibitors of β-lactamases, a key area of drug development.

The present invention will be further illustrated with reference to the following Example.

EXAMPLE 1

(i) The wells of a microtitre plate were individually filled with a total volume of 25 µl of a reaction mixture comprising an aqueous buffer solution of 100 mM Tris[hydroxymethyl]aminomethane hydrochloride ("Tris-HCl") and 10 mM magnesium chloride (pH 7.5), 75 µM UDP-MurNAc-L-alanine-γ-D-glutamic acid-m-diaminopimelic acid-D-alanine-D-alanine, 2.5 µM tritiated UDP-N-acetyl glucosamine (0.5 µCi per well), 4 µg of *Escherichia coli* AMA 1004 cell membranes and a solution of test compound (e.g. Tunicamycin, Vancomycin, Moenomycin, Penicillin G, Ampicillin, Cephaloridine and Bacitracin) of varying concentration in 4% dimethylsulphoxide. Tunicamycin is a known antagonist of the translocase enzyme, Vancomycin and Moenomycin are known antagonists of the transglycosylase enzyme, Penicillin G, Ampicillin and Cephaloridine are known antagonists of the transpeptidase enzyme and Bacitracin is a known antagonist of the lipid pyrophosphorylase.

Four wells of the microtitre plate were used as controls: two wells contained no UDP-N-acetylmuramylpentapeptide (0% reaction controls) and a further two wells contained no test compound (100% reaction controls).

The *E. coli* membranes were prepared in the following manner. Four to five colonies of the bacteria from an LB (Luria Bertani medium) agar plate were inoculated into 5 ml LB-broth and grown during the day (for 6–8 hours) at 37° C. In the evening 0.5 ml of this culture was used to inoculate 500 ml of LB-broth in a 2 l flask. The flask was incubated on a shaker at 30° C. overnight; typically an A600 of 2.0–2.5 was reached. Early the next morning this culture was used to inoculate 6 l of LB-broth (using 500 ml of LB-broth per 2 l flask) such that the starting A600 was 0.4–0.6. The culture was grown for 2 hours at 37° C. with vigorous shaking/aeration; the A600 reached was between 1.4 and 2.0. At this point the bacteria were cooled on ice and pelleted by centrifugation at 5,000×g for 15 minutes. The cell pellet was washed with 500 ml of Buffer A (50 mM Tris-HCl, pH 7.5/0.1 mM $MgCl_2$) and resuspended in a minimal volume (<20 ml) of Buffer A. The cells were lysed using the French Pressure cell. The cell lysate was spun at 3,500×g for 45 minutes. The supernatant was collected, diluted to 100 ml with Buffer A and ultra-centrifuged at 150,000×g for 45 minutes. The pellet from this spin was washed by resuspending it in 100 ml of Buffer A and re-centrifuging at 150,000×g for 30 minutes. This pellet was gently resuspended in a minimal volume (5–10 ml for 6 l culture) of Buffer A and frozen and stored in aliquots at −70° C. This is termed the membrane preparation and was used in the assay as a source of the peptidoglycan, five enzymes and undecaprenyl phosphate.

The microtitre plate was incubated at 37° C. for 1.5 hours and thereafter 5 µl of ethylenediaminetetraacetic acid (EDTA) was added to give a final EDTA concentration of is mM.

(ii) After addition of the EDTA, 170 µl of an aqueous suspension of wheatgerm agglutinin-coated scintillation proximity assay beads comprising 500 µg beads in a solution of Tris-HCl, pH 7.4, and t-octylphenoxypolyethoxyethanol ("Triton X-100", commercially sold by the Sigma-Aldrich Co. Ltd.) was added to each well such that the final concentration of Tris-HCl was 100 mM and that of Triton X-100 was 0.05%.

The plate was left for 3 hours at room temperature before being counted in the "Microbeta Trilux" counter.

What is claimed is:

1. An assay for detecting peptidoglycan synthesis, which comprises the steps of:
   (1) incubating a reaction mixture comprising in aqueous medium a uridine(5'-)diphosphate (UDP)-N-acetylmuramylpentapeptide, radiolabelled UDP-N-acetyl glucosamine, divalent metal ions, undecaprenyl phosphate, peptidoglycan, translocase enzyme, transferase enzyme, transglycosylase enzyme, transpeptidase enzyme and lipid pyrophosphorylase enzyme, under conditions that allow completion of peptidoglycan synthesis;
   (2) adding a divalent metal ion chelator compound to the reaction mixture of step (1) to terminate peptidoglycan synthesis;
   (3) adding lectin-coated beads impregnated with a fluorescer to the reaction mixture of step (2), which beads bind, via the lectin coating, the radiolabelled UDP-N-acetyl glucosamine in the peptidoglycan synthesized in step (1); and
   (4) measuring light energy emitted by the fluorescer as a result of activation of the fluorescer by the radiation energy emitted by the radiolabelled peptidoglycan proximately bound thereto, which light energy is indicative of the presence of radiolabeled peptidoglycan synthesized in step (1).

2. The assay according to claim 1, wherein the UDP-N-acetylmuramylpentapeptide is UDP-MurNAc-L-alanine-γ-D-glutamic acid-m-diaminopimelic acid-D-alanine-D-alanine.

3. The assay according to claim 1 or claim 2, wherein bacterial cell membranes provide one or morn of undecaprenyl phosphate, peptidoglycan, translocase enzyme, transferase enzyme, transglycosylase enzyme, transpeptidase enzyme and lipid pyrophosphorylase enzyme.

4. The assay according to claim 3, wherein the bacterial cell membranes are from *Escherichia coli*.

5. The assay according to claim 1, wherein the reaction mixture of step (1) further comprises a test compound.

6. The assay according to claim 5, wherein the test compound is an antagonist of one of the enzymes.

7. The assay according to claim 1, wherein ethylenediaminetetraacetic acid is used as the divalent metal ion chelator compound in step (2).

8. The assay according to claim 1, wherein the lectin-coated beads comprise wheat germ agglutinin.

* * * * *